(12) United States Patent
Lipton

(10) Patent No.: US 9,035,033 B2
(45) Date of Patent: May 19, 2015

(54) TUMOR AND INFECTIOUS DISEASE THERAPEUTIC COMPOSITIONS

(75) Inventor: James Spencer Lipton, Palm Beach, FL (US)

(73) Assignee: BIOMUNE, INC., Palm Beach, FL (US)

( * ) Notice: Subject to any disclaimer, the term of this patent is extended or adjusted under 35 U.S.C. 154(b) by 123 days.

(21) Appl. No.: 13/372,005

(22) Filed: Feb. 13, 2012

(65) Prior Publication Data

US 2012/0141560 A1     Jun. 7, 2012

Related U.S. Application Data

(63) Continuation of application No. 12/036,874, filed on Feb. 25, 2008, now Pat. No. 8,114,972, which is a continuation of application No. 10/991,049, filed on Nov. 17, 2004, now abandoned.

(60) Provisional application No. 60/520,503, filed on Nov. 17, 2003.

(51) Int. Cl.

| | | |
|---|---|---|
| *A61K 31/70* | (2006.01) |
| *A61K 38/20* | (2006.01) |
| *A61K 36/16* | (2006.01) |
| *A61K 36/185* | (2006.01) |
| *A61K 38/16* | (2006.01) |
| *A61K 45/06* | (2006.01) |

(52) U.S. Cl.
CPC ............. *A61K 38/2013* (2013.01); *A61K 36/16* (2013.01); *A61K 36/185* (2013.01); *A61K 38/16* (2013.01); *A61K 38/168* (2013.01); *A61K 45/06* (2013.01)

(58) Field of Classification Search
None
See application file for complete search history.

(56) References Cited

U.S. PATENT DOCUMENTS 5,919,464 A * 7/1999 Mann et al. ................ 424/278.1
6,103,243 A * 8/2000 Russell-Jones et al. . 424/195.11

OTHER PUBLICATIONS

Garson et al (J Neurosurg, 1981, 55(1): Abstract).*
Whitmore et al (Gene Therapy, 1996, 6: 1867-1875).*
Ueno et al. (J. Biomat. Sci. Polym. Ed. 1996; 7 (9): 753-8).*
Wooldridge et al (Blood, 1997, 89(8): 2994-2998).*

* cited by examiner

*Primary Examiner* — Sean Aeder
(74) *Attorney, Agent, or Firm* — Novak Druce Connolly Bove + Quigg LLP

(57) ABSTRACT

A pharmaceutical composition comprising lectins is anti-tumorigenic and anti-viral, bacterial or protozoan. The composition, termed BiOmune is also useful for imaging, diagnosis and therapy of cancer.

10 Claims, No Drawings

TUMOR AND INFECTIOUS DISEASE THERAPEUTIC COMPOSITIONS

CROSS REFERENCE TO RELATED APPLICATIONS

This Application is a continuation application of U.S. Continuation patent application Ser. No. 12/036,874, filed Feb. 25, 2008 entitled "TUMOR AND INFECTIOUS DISEASE THERAPEUTIC COMPOSITIONS", which is a continuation of U.S. patent application Ser. No. 10/991,049, filed Nov. 17, 2004, which claims priority to U.S. Provisional Patent Application No. 60/520,503, filed Nov. 17, 2003, the entirety of which are incorporated herein by reference.

FIELD OF THE INVENTION

The invention relates to compositions and methods for targeting and modulating the activity of tumor cells and cells infected by infectious disease agents. In particular, the invention relates to inhibition of immunoglobulin isoclass switching.

BACKGROUND

Cancer is one of the leading causes of disease, being responsible for 526,000 deaths in the United States each year. For example, breast cancer is the most common form of malignant disease among women in Western countries and, in the United States, is the most common cause of death among women between 40 and 55 years of age (Forrest, 1990). The incidence of breast cancer is increasing, especially in older women, but the cause of this increase is unknown. Malignant melanoma is another form of cancer whose incidence is, increasing at a frightening rate, at least sixfold in the United States since 1945, and is the single most deadly of all skin diseases.

One of the most devastating aspects of cancer is the propensity of cells from malignant neoplasms to disseminate from their primary site to distant organs and develop into metastases. Despite advances in surgical treatment of primary neoplasms and aggressive therapies, most cancer patients die as a result of metastatic disease. Animal tests indicate that about 0.01% of circulating cancer cells from solid tumors establish successful metastatic colonies.

Thus there is a need in the art to establish agents for therapy of cancer without the side effects observed with conventional therapies.

SUMMARY

Compositions for treatment of cancer and infectious diseases such as for example those associated with viral, bacterial, protozoan or fungal infections are described.

In a preferred embodiment, a composition comprising lectins is used to image, diagnose and treat cancers. A source of lectins includes, but is not limited to plants such as soybean, wheatgerm, mistletoe, and pokeweed. Preferably, these lectins are sensitive to the N-acetyl glucosamine epitope.

In a preferred embodiment, a therapeutic composition for treatment of cancer and/or infectious disease organisms comprises isolated and modified lectins; isolated and modified mitogens, interleukin, and or nucleic acids as identified by SEQ ID NO: 1. SEQ ID NO: 1 also includes variants, fragments or derivatives thereof. In addition, the nucleic acid composition can be replaced by poly (I:C) or added in combination with SEQ ID NO: 1. Preferably, the modified lectin is coupled to haptens, such as DNP. Any number of small molecules can be coupled to the lectin. Preferably, the lectins are coupled to small molecules with about 1 to about 10 small molecules.

In another preferred embodiment, the BiOmune composition comprises recombinant interleukins such as, recombinant Interleukin 2 (rIL-2) of about 100,000 U/kg.

In a preferred embodiment, the resultant composition comprises polyethylene glycol coated pokeweed mitogen (PWM-PEG) of about 10 µg PWM protein/kg; Helix pomatia lectin coupled to hapten DNP(HPL-DNP) of about 30 µg/HPL protein/kg and recombinant Interleukin 2 (rIL-2) of about 100,000 U/kg.

In another preferred embodiment, the BiOmune composition comprises a DNA nucleotide: GACGTCGACGT-TAACGTCAACGTT (SEQ ID NO: 1); DOTAP (1,2 dioleoyl-3-trimethylammonium-propane) and cholesterol. Alternatively, or in addition to, compound B comprises an equal weight of poly (I:C). The resulting composition is herein generically termed BiOmune and can comprise variations of molecules as disclosed herein.

In another preferred embodiment, the BiOmune compositions inhibit isoclass immunoglobulin switching. Inhibition of isoclass switching is important for the fixing of complement of targeted cells, i.e. those coated with immunoglobulin, preferably, IgM.

In another preferred embodiment, the lectins in the BiOmune compositions can be selected from at least one or combinations of lectins, such as: *Anguilla anguilla* (Eel serum); *Aleuria aurantia* (Orange peel fungus); *Agaricus bisporus* (Mushroom); *Amphicarpanea bracteata* (hog-peanut); *Hippaestrum hybrid* (Amaryllis bulbs); *Abrus precatorius* (Jequirity bean); *Bauhinia purpurea alba* (camel's foot tree); *Caragana arborescens* (Siberian pea tree); *Concanavalia ensiformis* (Jack bean); *Cicer arietinum* (chick pea); *Cytisus scoparius* (Scotch broom); *Colichos biflorus* (horse gram); *Datura stramonium* (Jimson weed, Thorn apple); *Erythrina crystagalli* (Coral tree); *Erythrina coralldendron* (Coral tree); *Euonymus europaeus* (spindle tree); *Dolichos biflorus* (horse gram); *Galanthus nivalis* (Snowdrop bulb); *Griffonia simplicifolia; Helix aspersa* (Garden snail); *Artocarpus integrifolia* (jackfruit); *Laburnum alpinum; Phaseolus lunatis* (also limensis) (Lima bean); *Lens culinaris* (lentil); *Lycopersicon esculentum* (Tomato); *Lathyrus oderatus* (Sweet pea); *Lotus tetragonolobus* (Asparagus pea); *Maackla amurensis* (maackla); *Maclura pomifera* (Osage orange); *Narcissus pseudonarcissus* (daffodil); *Phytolacca americana* (Pokeweed); *Phaseolis vulgaris* (Red kidney bean); *Arachis hypogaea* (Peanut); *Pisum sativum* (Pea); *Phytolacca americana* (pokeweed); *Psophocarpus tetagonolobus* (winged bean); *Psophocarpus tetagonolobus* (winged bean); *Ricinus communis* (Castor bean); *Robinia pseudoaccacia* (black locust); *Glycine max* (Soybean); *Sophora japonica* (Japanese pagoda tree); *Solanum tuberosum* (Potato); *Trichosanthes kinlowii* (China gourd); *Ulex europaeus* (Gorse or Furz seeds); *Viscum album* (European mistletoe); *Vicia faba* (Fava bean); *Vicia graminea; Vigna radiata* (mung bean); *Vicia saliva; Vicia villosa* (Hairy vetch); *Wisteria floribunda* (Japanese wisteria); *Triticum vulgaris* (Wheat germ); suc-WGA (Succinyl WGA).

In another preferred embodiment, isolated lectins stimulate B-lymphocytes and produces antibodies. Preferably the lectin is pokeweed mitogen (PWM). Not only is PWM a mitogen for B cells, it is an antigen that stimulates anti-PWM antibodies.

In a preferred embodiment, PWM delivery is engineered to target the tumor antigen, then produce an antibody 'bullet' to shoot at this target. Targeting to different antigens can also be achieved using a combination of lectins in the BiOmune composition.

In another preferred embodiment, the BiOmune compositions comprising lectins such as *helix pomatia* can be used in conjunction with chemotherapeutic agents. The BiOmune composition can be administered to a patient in combination with metronomic therapy. For example, administration of continuous low-doses of the chimeric fusion molecule and one or more therapeutic agents. Therapeutic agents can include, for example, chemotherapeutic agents such as, cyclophosphamide (CTX, 25 mg/kg/day, p.o.), taxanes (paclitaxel or docetaxel), busulfan, cisplatin, cyclophosphamide, methotrexate, daunorubicin, doxorubicin, melphalan, cladribine, vincristine, vinblastine, and chlorambucil.

Other aspects of the invention are describe infra.

DETAILED DESCRIPTION

The invention provides compositions and methods for treating cancer and disease caused by infectious disease organisms. In particular, the compositions are found to inhibit isoclass switching from IgM to IgG. The below described preferred embodiments illustrate adaptations of these compositions and methods. Nonetheless, from the description of these embodiments, other aspects of the invention can be made and/or practiced based on the description provided below.

Before the present invention is disclosed and described, it is to be understood that this invention is not limited to the particular structures, process steps, or materials disclosed herein, but is extended to equivalents thereof as would be recognized by those ordinarily skilled in the relevant arts. It, should also be understood that terminology employed herein is used for the purpose of describing particular embodiments only and is not intended to be limiting.

DEFINITIONS

In accordance with the present invention and as used herein, the following terms are defined with the following meanings, unless explicitly stated otherwise.

As used herein, "a", "an," and "the" include plural references unless the context clearly dictates otherwise.

The term "biomolecule" refers to DNA, RNA (including mRNA, rRNA, tRNA and tmRNA), nucleotides and nucleosides.

A base "position" as used herein refers to the location of a given base or nucleotide residue within a nucleic acid.

A "nucleic acid of interest," as used herein, is any particular nucleic acid one desires to study in a sample.

The term "nucleic acid" may refer either to a molecule of DNA of indeterminate length or to a molecule of RNA of indeterminate length. In some aspects of the invention biomolecules and/or nucleic acids may be produced using a variety of known techniques, however, the preferred technique is rolling-circle amplification (RCA). Other techniques may include, for example, polymerase chain reaction (PCR) amplification, reverse-transcriptase polymerase chain reaction (RT-PCR) amplification, oligo ligation amplification (OLA), or single nucleotide primer extension reaction (SNuPE). Such techniques are well known to one skilled in the art and further are described in laboratory manuals such as Sambrook et al, ("Molecular Cloning: A Laboratory Manual", Third edition, Cold Spring Harbor Laboratory, 2001) or Ausubel et al. ("Current Protocols in Molecular Biology", John Wiley & Sons, 1998) both of which are incorporated herein by reference, including any drawings, figures or tables.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element.

Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

As used herein, the term "administering a molecule to a cell" (e.g., an expression vector, nucleic acid, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "Tm" is used in reference to the "melting temperature". The melting temperature is the temperature at which 50% of a population of double-stranded nucleic acid molecules becomes dissociated into single strands. The equation for calculating the Tm of nucleic acids is well-known in the art. The Tm of a hybrid nucleic acid is often estimated using a formula adopted from hybridization assays in 1 M salt, and commonly used for calculating Tm for PCR primers: Tm=[(number of A+T)×2° C.+(number of G+C)×4° C.]. C. R. Newton et al. PCR, 2nd Ed., Springer-Verlag (New York: 1997), p. 24. This formula was found to be inaccurate for primers longer that 20 nucleotides. Other more sophisticated computations exist in the art which take structural as well as sequence characteristics into account for the calculation of Tm. A calculated Tm is merely an estimate; the optimum temperature is commonly determined empirically.

"Transcriptional regulatory sequence" is a generic term used throughout the specification to refer to DNA sequences, such as initiation signals, enhancers, promoters, silencing elements, which induce, inhibit or control transcription of protein coding sequences with which they are operably linked.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A vector is a composition which can transduce, transfect, transform or infect a cell, thereby causing the cell to express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell.

"Label molecules" are chemical or biochemical moieties used for labeling a polynucleotide, a polypeptide, or an antibody. They include, but are not limited to, radionuclides, enzymes, substrates, cofactors, inhibitors, fluorescent agents, chromogenic agents, chemiluminescent agents, magnetic particles, and the like. Reporter molecules specifically bind, establish the presence of, and allow quantification of a particular polynucleotide, polypeptide, or antibody.

"Sample" is used herein in its broadest sense. A sample suspected of containing a nucleic acid can comprise a cell, chromosomes isolated from a cell (e.g., a spread of metaphase chromosomes), genomic DNA, RNA, cDNA and the like. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

The terms "nucleic acid molecule" or "polynucleotide" will be used interchangeably throughout the specification, unless otherwise specified. As used herein, "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

Homologous nucleic acid sequences, when compared, exhibit significant sequence identity or similarity. The standards for homology in nucleic acids are either measures for homology generally used in the art by sequence comparison or based upon hybridization conditions. The hybridization conditions are described in greater detail below.

As used herein, "substantial homology" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a fragment derived from a known molecule. Typically, selective hybridization will occur when there is at least about 55% homology over a stretch of at least about 14 nucleotides, preferably at least about 65%, more preferably at least about 75%, and most preferably at least about 90%. See Kanehisa (1984) *Nuc. Acids Res.* 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The endpoints of the segments may be at many different pair combinations.

As used herein, the terms "complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma.

Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic). Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Examples of sarcomas which can be treated with the compositions and optionally a potentiator and/or chemotherapeutic agent include, but not limited to a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the compositions and optionally a potentiator and/or another chemotherapeutic agent include but not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the compositions and optionally a potentiator and/or a chemotherapeutic agent include but not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

A "detectable marker gene" is a gene that allows cells carrying the gene to be specifically detected (e.g., distinguished from cells which do not carry the marker gene). A large variety of such marker genes are known in the art. Preferred examples thereof include detectable marker genes which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., WO 92/08796, published May 29, 1992, and WO 94/28143, published Dec. 8, 1994). Such marker genes can provide an added measure of control that can be advantageous in gene therapy contexts.

As used herein, the term "gene" means the gene and all currently known variants thereof and any further variants which may be elucidated.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The term "variant," when used in the context of a polynucleotide sequence, may encompass a polynucleotide sequence related to a wild type gene. This definition may also include, for example, "allelic", "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides.

Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

"Diagnostic" or "diagnosed" means identifying the presence or nature of a pathologic condition or a patient susceptible to a disease. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The treatment of neoplastic disease or neoplastic cells, refers to an amount of the composition, vectors and/or peptides, described throughout the specification and in the Examples which follow, capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention of tumor cell infiltration into peripheral organs; (6) inhibition, including (i) reduction, (ii) slowing down or (iii) complete prevention of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

Treatment of an individual suffering from an infectious disease organism refers to a decrease and elimination of the disease organism from an individual. For example, a decrease of viral particles as measured by plaque forming units or other automated diagnostic methods such as ELISA etc.

As used herein "immunogenicity modifier" refers to a decreased immune recognition against an antigen, i.e. a non-immunogenic antigen.

The Composition Termed BiOmune

The BiOmune composition comprises isolated lectins and/or isolated and modified lectins; isolated mitogens and/or isolated and modified mitogens, interleukin, and or nucleic acids as identified by SEQ ID NO: 1. SEQ ID NO: 1 also includes variants, fragments or derivatives thereof. In addition, the nucleic acid composition can be replaced by poly (I:C) or added in combination with SEQ ID NO: 1. Any combination of the above can be included in the composition.

As a non-limiting example, the composition is as follows. *Helix pomatia* lectin, was modified using 2,4-dinitrophenol (DNP). Modification was by coupling of DNP to the soluble protein. (Inman, J. K. et al., *Immunochemistry,* 10:165, 1973). A solution of 300 mg of *Helix pomatia* lectin in 4.0 ml of 0.25 M potassium borate was cooled to 0° C. fifty seven micromoles (28.6 mg of N-(2,4-dinitrophenyl-β-alanylglycylglycine Boc hydrazide (compound "J") were converted to the corresponding acyl azide by reaction with nitrous acid in cold dimethylformamide after removal of the Boc group.

After addition of sulfamic acid to destroy nitrous acid, the azide solution was added to the cold buffered *Helix pomatia*. The mixture was stirred at 0° C. for 2 days and dialyzed in the cold for 2 days against 0.1 M NaCl and 2 days against water. Outside solutions were saturated with toluene. The dialysate was lyophilized.

The resulting *Helix pomatia* lectin has about 10 DNP molecules attached to primarily lysine residues in the lectin molecule. This hapten conjugate was added to compound A. Compound A comprises isolated pokeweed mitogen which is coated with polyethylene glycol as described in U.S. patent application Ser. No. 09/983,129 which is incorporated herein by reference in its entirety. Compound A optionally comprises recombinant Interleukin 2 (rIL-2) of about 100,000 U/kg.

The resultant composition comprises polyethylene glycol coated pokeweed mitogen (PWM-PEG) of 10 µg PWM protein/kg; Helix pomatia lectin coupled to hapten DNP(HPL-DNP) of 30 µg/HPL protein/kg and recombinant Interleukin 2 (rIL-2) of 100,000 U/kg.

Compound B comprises a DNA nucleotide: GACGTCGACGTTAACGTCAACGTT (SEQ ID NO: 1); DOTAP (1,2 dioleoyl-3-trimethylammonium-propane) and cholesterol.

Compound B is prepared as follows. DNA (SEQ ID NO: 1) is added to cationic lipids DOTAP and cholesterol in a 1:1 molar ratio. The DNA is added at a ratio of 30 nmol lipid to 1 µg DNA to a final concentration of 100 µg DNA per 0.1 ml dextrose. The dose of DNA used for immunostimulation is about 50-100 µg/kg. Alternatively, or in addition to, compound B comprises an equal weight of poly (I:C).

The resulting composition is herein termed BiOmune. The lectins in the BiOmune compositions can include Helix pomatia and at least one other lectin, or any other lectin that can be selected based on the disease to be treated as described infra.

In a preferred embodiment, the compositions are highly cytotoxic for tumors, specific for tumor antigens only and, universal for all tumor antigens.

In another preferred embodiment, the composition inhibits the life cycle of an infectious disease organism.

In another preferred embodiment, the composition inhibits isoclass switching and results in the lysis of tumor cells and/or cells infected with an infectious disease organism. Without wishing to be bound by theory, antigen specific IgM detects abnormal antigens, fixes complement with a higher efficiency than IgG and initiates the complement cascade thereby resulting in the lysis of such cells.

In another preferred embodiment, the composition comprises a nucleic acid sequence identified by SEQ ID NO: 1. Preferably, the nucleic acid sequence includes derivatives, fragments and variants of SEQ ID NO: 1.

In another preferred embodiment, the composition comprises poly (I:C) which can replace SEQ ID NO: 1 or added in addition to the nucleic acid sequence, in equal weight.

In another preferred embodiment, the BiOmune composition comprises one or more isolated lectins. Examples of lectins in addition to lectins isolated from Helix pomatia include but not limited to: Anguilla anguilla (Eel serum); Aleuria aurantia (Orange peel fungus); Agaricus bisporus (Mushroom); Amphicarpanea bracteata (hog-peanut); Hippaestrum hybrid (Amaryllis bulbs); Abrus precatorius (Jequirity bean); Bauhinia purpurea alba (camel's foot tree); Caragana arborescens (Siberian pea tree); Concanavalia ensiformis (Jack bean); Cicer arietinum (chick pea); Cytisus scoparius (Scotch broom); Colichos biflorus (horse gram); Datura stramonium (Jimson weed, Thorn apple); Erythrina crystagalli (Coral tree); Erythrina coralldendron (Coral tree); Euonymus europaeus (spindle tree); Dolichos biflorus (horse gram); Galanthus nivalis (Snowdrop bulb); Griffonia simplicifolia; Helix aspersa (Garden snail); Artocarpus integrifolia (jackfruit); Laburnum alpinum; Phaseolus lunatis (also limensis) (Lima bean); Lens culinaris (lentil); Lycopersicon esculentum (Tomato); Lathyrus oderatus (Sweet pea); Lotus tetragonolobus (Asparagus pea); Maackla amurensis (maackla); Madura pomifera (Osage orange); Narcissus pseudonarcissus (daffodil); Phytolacca americana (Pokeweed); Phaseolis vulgaris (Red kidney bean); Arachis hypogaea (Peanut); Pisum sativum (Pea); Phytolacca americana (pokeweed); Psophocarpus tetagonolobus (winged bean); Psophocarpus tetagonolobus (winged bean); Ricinus communis (Castor bean); Robinia pseudoaccacia (black locust); Glycine max (Soybean); Sophora japonica (Japanese pagoda tree); Solanum tuberosum (Potato); Trichosanthes kinlowii (China gourd); Ulex europaeus (Gorse or Furz seeds); Viscum album (European mistletoe); Vicia faba (Fava bean); Vicia graminea; Vigna radiata (mung bean); Vicia saliva; Vicia villosa (Hairy vetch); Wisteria floribunda (Japanese wisteria); Triticum vulgaris (Wheat germ); Succinyl WGA.

In accordance with the invention any one or more, or combinations thereof with Helix pomatia can be used in the composition of the inventions. Optionally, the lectins can be modified with desired haptens such as for example, DNP as described in the Examples which follow.

Inhibition of Immunoglobulin Isoclass Switching

In a preferred embodiment, the compositions inhibit class switching of IgM to IgG. Macroglobulin, or immunoglobulin-M, is generated by the B1 lymphocyte independent of the T lymphocyte. It is also the first class of globulins made when T and B-lymphocytes interact, but it is quickly replaced by gamma globulin in a process called "isoclass switching." The most dramatic forms of tissue rejection, such as the blood group incompatibility reaction and hyperacute xenograft rejection, are mediated by macroglobulins. The main advantages of the invention is that by inhibiting isoclass switching from IgM to IgG, the complement cascade is efficiently activated. It takes at least two molecules of IgG to fix the first molecule of complement (C1q). In contrast, a single molecule of IgM can fix C1q and initiate the complement cascade leading to the lysis of the cell.

IgM antibodies are capable of destroying a 'foreign' cell. Since there are multiple tumor antigens, all with differing protein structure, an antibody specific for one would necessarily be wrong for the others but what conventional wisdom misses is that tumor antigens are not just proteins; they are glycoproteins.

The issue is—Is there a common sugar structure present on the surface of cancer cells? A class of lectins found in plants, such as soybean, wheatgerm, mistletoe, and pokeweed can label cancerous cells and, in some cases, slow down their growth. These lectins bind to a repeating sugar linkage called N-acetyl glucosamine. This can be found on tumor markers such as CEA, PSA, HER2.

In another preferred embodiment, the compositions minimize the amount of IgG formed. Unmodified PWM produces IgG and IgM in roughly equivalent amounts. Modification with polyethylene glycol or dinitrophenol decreases IgG production. We were able to substantially decrease IgG production by coating 50% of the molecule with PEG.

Even though the initial production of IgG was low with PEG, eventually isoclass switching occurs and IgG production rises again. Ultimately we were able to abolish switching by using a small nucleotide as defined by SEQ ID NO: 1.

Tumor and Infectious Disease Therapy

In accordance with the invention target cells, either prokaryotic and eukaryotic, are selectively targeted by the compositions by, for example, inclusion of antibodies specific for an antigen. Infectious disease almost invariably results in the acquisition of foreign nucleic acids, which could be targeted using this technology. Specific targets could be viral, e.g. HIV (virus or provirus) or bacterial, e.g. multi-drug resistant bacteria e.g. TB, fungal or protozoan. This technology can be especially useful in treating infections for which there is no effective anti-microbial or anti-viral agent (e.g. Ebola virus, etc.), or known or novel bio-terrorist agents.

The invention may be used against protein coding gene products as well as non-protein coding gene products. Examples of non-protein coding gene products include gene products that encode ribosomal RNAs, transfer RNAs, small nuclear RNAs, small cytoplasmic RNAs, telomerase RNA, RNA molecules involved in DNA replication, chromosomal rearrangement and the like.

In another preferred embodiment, abnormal or cancer cells are targeted by the BiOmune compositions. For example, many malignancies are associated with the presence of foreign DNA, e.g. Bcr-Abl, Bcl-2, HPV, and these provide unique molecular targets e.g. antigens, to permit selective malignant cell targeting. The approach can be used to target expression products as a result of single base substitutions (e.g. K-ras, p53) or methylation changes. However, proliferation of cancer cells may also be caused by previously unexpressed gene products. These gene sequences can be targeted, thereby, inhibiting further expression and ultimate death of the cancer cell. In other instances, transposons can be the cause of such deregulation and transposon sequences can be targeted, e.g. Tn5.

According to the present invention, the BiOmune compositions can be designed to be specific for a molecule, which either causes, participates in, or aggravates a disease state, in a patient. See for example Table 6 wherein suitable lectins can be included for specific microorganism targets. For example, in a viral infection, targets include molecules responsible for viral replication; a viral infection cycle, such as, for example, attachment to cellular ligands; viral gene products encoding host immune modulating functions. Particularly preferred viral organisms causing human diseases according to the present invention include (but not restricted to) Filoviruses, Herpesviruses, Hepatitisviruses, Retroviruses, orthomyxoviruses, Paramyxoviruses, Togaviruses, Picornaviruses, Papovaviruses and Gastroenteritisviruses. Other preferred, non-limiting examples of viral agents are listed in Table 1.

According to another preferred embodiment of the invention, the compositions are useful in the treatment of human or domestic animal bacterial pathogens. Particularly preferred bacteria causing serious human diseases are the Gram positive organisms: *Staphylococcus aureus, Staphylococcus epidermidis, Enterococcus faecalis* and *E. faecium, Streptococcus pneumoniae* and the Gram negative organisms: *Pseudomonas aeruginosa, Burkholdia cepacia, Xanthomonas maltophila, Escherichia coli, Enterobacter* spp, *Klebsiella pneumoniae* and *Salmonella* spp. The target molecules may include (but are not restricted to) molecules essential to bacterial survival and multiplication in the host organism, virulence gene products, gene products encoding single- or multi-drug resistance. However, gram negative bacteria are also within the scope of the invention.

According to one preferred embodiment of the invention, the compositions are used to treat against protozoa infecting humans and causing human diseases. Particularly preferred protozoan organisms causing human diseases according to the present invention include (but not restricted to) Malaria e.g. *Plasmodium falciparum* and *M. ovale*, Trypanosomiasis (sleeping sickness) e.g. *Trypanosoma cruzei*, Leischmaniasis e.g. *Leischmania donovani*, Amebiasis e.g. *Entamoeba histolytica*.

According to another preferred embodiment of the invention, the compositions are used to treat against fungi causing pathogenic infections in humans. Particularly preferred fungi causing or associated with human diseases according to the present invention include (but not restricted to) *Candida albicans, Histoplasma neoformans, Coccidioides immitis* and *Penicillium marneffei*.

The invention in general provides a method for treating diseases, such as cancer and diseases which are caused by infectious agents such as viruses, bacteria, intra- and extracellular parasites, insertion elements, fungal infections, etc., which may also cause expression of gene products by a normally unexpressed gene, abnormal expression of a normally expressed gene or expression of an abnormal gene.

The methods of the invention are preferably employed for treatment or prophylaxis against diseases caused abnormal cell growth and by infectious agents, particularly for treatment of infections as may occur in tissue such as lung, heart, liver, prostate, brain, testes, stomach, intestine, bowel, spinal cord, sinuses, urinary tract or ovaries of a subject. The methods of the invention also may be employed to treat systemic conditions such as viremia or septicemia. The methods of the invention are also preferably employed for treatment of diseases and disorders associated with viral infections or bacterial infections, as well as any other disorder caused by an infectious agent.

Examples of viral organisms include, but not restricted to, those listed in table 1. For information about the viral organisms see Fields of Virology, 3. ed., vol 1 and 2, BN. Fields et al. (eds.). Non-limiting examples of targets of selected viral organisms are listed in table 2.

TABLE 1

Selected viral organisms causing human diseases.

| | |
|---|---|
| Herpesviruses | Alpha-herpesviruses: |
| | Herpes simplex virus 1 (HSV-1) |
| | Herpes simplex virus 2 (HSV-2) |
| | Varicella Zoster virus (VZV) |
| | Beta-herpesviruses: |
| | Cytomegalovirus (CMV) |
| | Herpes virus 6 (HHV-6) |
| | Gamma-herpesviruses: |
| | Epstein-Barr virus (EBV) |
| | Herpes virus 8 (HHV-8) |
| Hepatitis viruses | Hepatitis A virus |
| | Hepatitis B virus |
| | Hepatitis C virus |
| | Hepatitis D virus |
| | Hepatitis E virus |
| Retroviruses | Human Immunodeficiency 1 (HIV-1) |
| Orthomyxoviruses | |
| | Influenzaviruses A, B and C |
| Paramyxoviruses | Respiratory Syncytial virus (RSV) |
| | Parainfluenza viruses (PI) |
| | Mumps virus |
| | Measles virus |
| Togaviruses | Rubella virus |
| Picornaviruses | Enteroviruses |
| | Rhinoviruses |
| | Coronaviruses |
| Papovaviruses | Human papilloma viruses (HPV) |
| | Polyomaviruses (BKV and JCV) |
| Gastroenteritisviruses | |
| Filoviridae | |
| Bunyaviridae | |
| Rhabdoviridae | |
| Flaviviridae | |

TABLE 2

Target gene products of viral organisms

| Organism | target gene | open reading frame | gene product |
|---|---|---|---|
| HIV | gag: | MA | p17 |
| | | CA | p24 |

TABLE 2-continued

Target gene products of viral organisms

| Organism | target gene | open reading frame | gene product |
|---|---|---|---|
| | | NC | p7 |
| | | | p6 |
| | pol: | PR | p15 |
| | | RT | p66 |
| | | | p31 |
| | env: | | gp120 |
| | | | gp41 |
| | tat | | transcriptional transactivator |
| | rev | | regulator of viral expression |
| | vif | | |
| | vpr | | |
| | vpu | | |
| | nef | | |
| RSV | NS1 | | |
| | NS2 | | |
| | L | | |
| | 2-5A-dependent Rnase L | | |
| HPV | E1 | | helicase |
| | E2 | | transcription regulator |
| | E3 | | |
| | E4 | | late NS protein |
| | E5 | | transforming protein |
| | E6 | | transforming protein |
| | E7 | | transforming protein |
| | E8 | | |
| | L1 | | major capsid protein |
| | L2 | | minor capsid protein |
| HCV | NS3 | | protease |
| | NS3 | | helicase |
| | HCV-IRES | | |
| | NS5B | | polymerase |
| HCMV | DNA polymerase | | |
| | IE1 | | |
| | IE2 | | |
| | UL36 | | |
| | UL37 | | |
| | UL44 | | polymerase asc. protein |
| | UL54 | | polymerase |
| | UL57 | | DNA binding protein |
| | UL70 | | primase |
| | UL102 | | primase asc. protein |
| | UL112 | | |
| | UL113 | | |
| | IRS1 | | |
| VZV | | 6 | |
| | | 16 | |
| | | 18 | |
| | | 19 | |
| | | 28 | |
| | | 29 | |
| | | 31 | |
| | | 39 | |
| | | 42 | |
| | | 45 | |
| | | 47 | |
| | | 51 | |
| | | 52 | |
| | | 55 | |
| | | 62 | |
| | | 71 | |
| HSV | IE4 | | US1 |
| | IE5 | | US12 |
| | IE110 | | ICP0 |
| | IE175 | | ICP4 |
| | UL5 | | helicase |
| | UL8 | | helicase |
| | UL13 | | capsid protein |
| | UL30 | | polymerase |
| | UL39 | | ICP6 |
| | UL42 | | DNA binding protein |

Information about the above selected gene products, open reading frames and gene products is found in the following references: Field A. K. and Biron, K. K. "The end of innocence" revisited: resistance of herpesviruses to antiviral drugs. *Clin. Microbiol. Rev.* 1994; 7: 1-13. Anonymous. Drug resistance in cytomegalovirus: current knowledge and implications for patient management. *J. Acquir. Immune Defic. Syndr. Hum. Retrovir.* 1996; 12: S1-SS22. Kelley R et al. Varicella in children with perinatally acquired human immunodeficiency virus infection. *J Pediatr* 1994; 124: 271-273. Hanecak et al. Antisense oligonucleotides inhibition of hepatitis C virus, gene expression in transformed hepatocytes. *J Virol* 1996; 70: 5203-12. Walker Drug discovery Today 1999; 4: 518-529. Zhang et al. Antisense oligonucleotides inhibition of hepatitis C virus (HCV) gene expression in livers of mice infected with an HCV-Vaccinia virus recombinant. *Antim. Agents Chemotherapy* 1999; 43, 347-53. Feigin R D, Chemy J D, eds. Textbook of pediatric infectious diseases. Philadelphia: WB Saunders, 1981. Chen B. et al., Induction of apoptosis of human cervical carcinoma cell line SiHa by antisense oligonucleotide of human papillomavirus type 16 E6 gene. 2000; 21(3): 335-339. The human herpesviruses. New York: Raven Press; 1993. DeClerque E, Walker R T, eds. Antiviral drug development: a multi-disciplinary approach. Plenum; 1987. Antiviral Drug Resistance (Richman, D. D., ed.), Wiley, Chichester, 1995. Flint S J et al. eds. Principles of virology: Molecular biology, pathogene product and control.

It should be appreciated that in the above table 2, an indicated gene means the gene and all currently known variants thereof, including the different mRNA transcripts that the gene and its variants can give rise to, and any further gene variants which may be elucidated. In general, however, such variants will have significant sequence identity to a sequence of table 2 above, e.g. a variant will have at least about 70 percent sequence identity to a sequence of the above table 2, more typically at least about 75, 80, 85, 90, 95, 97, 98 or 99 percent sequence identity to a sequence of the above table 2. Sequence identity of a variant can be determined by any of a number of standard techniques such as a BLAST program http://www.ncbi.nlm.nih.gov/blast/).

Sequences for the gene products listed in Table 2 can be found in GenBank (http://www.ncbi.nlm.nih.gov/). The gene sequences may be genomic, cDNA or mRNA sequences. Preferred sequences are viral gene products containing the complete coding region and 5' untranslated sequences that are involved in viral replication.

Bacterial Infections:

According to another preferred embodiment of the invention, the compositions are used to treat against human or domestic animal bacterial pathogens listed in (but not restricted to) table 3. Gene products essential to bacterial survival and multiplication in the host organism, virulence gene products encoding single- or multi-drug resistance such as for instance the gene products listed in table 4.

TABLE 3

Selected bacteria causing serious human diseases

| Gram positive organisms: | *Staphylococcus aureus*: strains include methicillin resistant (MRSA), methicillin-vancomycin resistant (VMRSA) and vancomycin intermediate resistant (VISA). *Staphylococcus epidermidis*. *Enterococcus faecalis* and *E. faecium*: strains include vancomycin resistant (VRE). *Streptococcus pneumoniae*. |
|---|---|

TABLE 3-continued

Selected bacteria causing serious human diseases

Gram negative organisms: Pseudomonas aeruginosa.
Burkholdia cepacia.
Xanthomonas maltophila.
Escherichia coli
Enterobacter spp.
Klebsiella pneumoniae
Salmonella spp.

REFERENCES

Cookson B. D., Nosocomial antimicrobial resistance surveillance. *J. Hosp. Infect.* 1999:97-103. Richards M. J. et al. Nosocomial infections in medical intensive care units in the United States. National Nosocomial Infections Surveillance System. *Crit. Care. Med.* 1999; 5:887-92. House of Lords Select Committee on Science and Technology. Resistance to antibiotics and other antimicrobial agents. London: 1998; Her Majesty's Stationary Office. Johnson A. P. Intermediate vancomycin resistance in *S. aureus*: a major threat or a minor inconveniance? *J. Antimicrobial. Chemother.* 1998; 42:289-91. Baquero F. Pneumococcal resistance to beta-lactam antibiotics: a global overview. *Microb. Drug Resist.* 1995; 1:115-20. Hsueh P. R. et al. Persistence of a multidrug resistant *Pseudomonas aeruginosa* clone in an intensive care burn unit. *J. Clin. Microbiol.* 1998; 36:1347-51. Livermore D. Multiresistance and Superbugs. *Commun. Dis. Public Health* 1998; 1:74-76.

TABLE 4

Examples of virulence gene products in bacteria.

| | |
|---|---|
| Protein synthesis targets | Translation initiation factors (e.g. IF1, IF2, IF3) Translation elongation factors (e.g. EF-Tu, EF-G) Translation release factors (RF1, RF2, RF3) |
| Cell wall synthesis | Penicillin binding proteins (e.g. PB.P.1 to PB.P.9) |
| Cell division | Proteins encoded by the ftsQAZ operon |
| Nucleic acid synthesis | Gyrases, Sigma 70 and Helicase |
| Virulence | Ureases |

REFERENCES

*Escherichia coli* and *Salmonella* in Cellular and Molecular Biology, vol 1 & 2. C Neidhardt and R Curtiss (eds.), American Society for Microbiology Press. Gram-Positive Pathogens. V A Fischetti et al. (eds.), American Society for Microbiology Press. Bacterial Pathogene productsis: A Molecular Approach. A A Salyers and D D Whitt (eds.), American Society for Microbiology Press. Organization of the Procaryotic Genome. R L Charlebois (ed.), American Society for Microbiology Press.

Listed in Table 5 below are examples of genes encoding the protein complexes listed in Table 4 above. The individual genes have homologues in the major human pathogenic bacteria listed in Table 3. Table 5 below depicts an example of a Gram negative (*Escherichia coli*) and a Gram positive (*Staphylococcus aureus*) organism, chosen as representatives for the two groups of bacteria.

TABLE 5

Examples of gene products.

| Target group | E. coli | S. aureus |
|---|---|---|
| Protein synthesis | prfA | prfA |
| | prfB | |
| | prfC | prfC |
| | infA | infA |
| | infB | infB |
| | infC | |
| | tufA | tuf |
| | fusA | fus |
| Cell wall synthesis | mrcA | pb.p.A |
| | mrcB | pb.p.2 |
| | pb.p.B | fmhB |
| | | femA |
| | | femB |
| Cell division | ftsA | ftsA |
| | ftsQ | |
| | ftsZ | ftsZ |
| Nucleic acid synthesis | gyrA | pcrC |
| | gyrB | |
| | rpoD | |

REFERENCES

*Escherichia coli* and *Salmonella* in Cellular and Molecular Biology, vol 1 & 2. C Neidhardt and R Curtiss (eds.), American Society for Microbiology Press. Gram-Positive Pathogens. V A Fischetti et al. (eds.), American Society for Microbiology Press. Bacterial. Pathogenesis: A Molecular Approach. A A Salyers and D D Whitt (eds.), American Society for Microbiology Press. Organization of the Prokaryotic Genome. R L Charlebois (ed.), American Society for Microbiology Press.

It should be appreciated that in the above table 4 and 5, an indicated gene means the gene and all currently known variants thereof, including the different mRNA transcripts that the gene and its variants can give rise to, and any further gene variants which may be elucidated. In general, however, such variants will have significant sequence identity to a sequence of table 4 and 5 above, e.g. a variant will have at least about 70 percent sequence identity to a sequence of the above table 4 and 5, more typically at least about 75, 80, 85, 90, 95, 97, 98 or 99 percent sequence identity to a sequence of the above table 5 and 6. Sequence identity of a variant can be determined by any of a number of standard techniques such as a BLAST program http://www.ncbi.nlm.nih.gov/blast/).

Sequences for the gene products listed in Table 4 and 5 can be found in GenBank (http://www.ncbi.nlm.nih.gov/). The gene sequences may be genomic, cDNA or mRNA sequences.

Protozoan Infections:

According to one preferred embodiment of the invention, the compositions are used useful for treating against protozoan organisms infecting humans and causing human diseases. Such protozoa include, but are not restricted to, the following: 1. Malaria e.g. *Plasmodium falciparum* and *M. ovale*. (references: Malaria by M Wahlgren and P Perlman (eds.), Harwood Academic Publishers, 1999. Molecular Immunological Considerations in Malaria Vaccine Development by M F Good and A J Saul, CRC Press 1993). 2. Trypanosomiasis (sleeping sickness) e.g. *Trypanosoma cruzei* (reference: Progress in Human African Trypanosomiasis, Sleeping Sickness by M Dumas et al. (eds.), Springer Verlag 1998). 3. Leischmaniasis e.g. *Leischmania donovani* (reference. A L Banuals et al., Molecular Epidemiology and Evolutionary Genetics of *Leischmania* Parasites. *Int J Parasitol* 1999; 29:1137-47). 4. Amebiasis e.g. *Entamoeba his-*

*tolytica* (R P Stock et al., Inhibition of Gene Expression in *Entamoeba histolytica* with Antisense Peptide Nucleic Acid Oligomers. *Nature Biotechnology* 2001; 19:231-34).

Fungal Infections:

According to one preferred embodiment of the invention, the compositions are used to treat against fungi causing pathogenic infections in humans. These include, but are not restricted to, the following: *Candida albicans* (references: A H Groll et al., Clinical pharmacology of systemic antifungal agents: a comprehensive review of agents in clinical use, current investigational compounds, and putative targets for antifungal drug development. *Adv. Pharmacol.* 1998:44:343-501. M D D Backer et al., An antisense-based functional genomics approach for identification of gene products critical for growth of *Candida albicans. Nature Biotechnology* 2001; 19:235-241) and others, e.g., *Histoplasma neoformans, Coccidioides immitis* and *Penicillium* marneffei (reference: S A Marques et al., Mycoses associated with AIDS in the Third World. Med Mycol 2000; 38 Suppl. 1:269-79).

Host Cellular Gene Products Involved in Viral Diseases:

Besides gene products encoded by viruses for their replication, the initial step to infection is binding to cellular ligands. For example CD4, chemokine receptors such as CCR3, CCR5 are required for HIV infection. Furthermore, viruses also upregulate certain chemokines which, aid in their replication, for example in the case of HIV there is an increase in IL-2 which results in an increase of $CD4^+$ T cells, allowing for an increase in the pool of cells for further infection in the early stages of the disease. The compositions may be used to prevent any further upregulation of gene products that may aid in the infectivity and replication rate of the viruses.

In another preferred embodiment, the compositions can be used in treating diseases wherein immune cells are involved in the disease, such as autoimmune disease; hypersensitivity to allergans; organ rejection; inflammation; and the like. Examples of inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis, dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity. Examples of autoimmune diseases include, but are not limited to psoriasis, Type I diabetes, Reynaud's syndrome, autoimmune thyroiditis, EAE, multiple sclerosis, rheumatoid arthritis and lupus erythematosus.

Viral Vectors

In a preferred embodiment, the compositions of the invention can be tailored to include a nucleic acid sequence (e.g., SEQ ID NO: 1, derivatives, fragments and variants thereof) in an expression vector. Various techniques using other vectors such as, viral vectors for the introduction of an inhibitor of immunoglobulin isoclass switching, into a cell may be utilized in the methods of the invention. Viral vectors for use in the invention are those that exhibit low toxicity to a host cell. Viral vector methods and protocols that may be used in the invention are reviewed in Kay et al. *Nature Medicine* 7:33-40, 2001. The use of specific vectors, including those based on adenoviruses, adeno-associated viruses, herpes viruses, and retroviruses are described in more detail below.

The use of recombinant adenoviruses as vectors is discussed in W. C. Russell, *Journal of General Virology* 81:2573-2604, 2000; and Bramson et al., *Curr. Opin. Biotechnol.* 6:590-595, 1995. Adenovirus vectors are preferred for use in the invention because they (1) are capable of highly efficient gene expression in target cells and (2) can accommodate a relatively large amount of heterologous (non-viral) DNA. A preferred form of recombinant adenovirus is a "gutless, "high-capacity", or "helper-dependent" adenovirus vector. Such a vector features, for example, (1) the deletion of all or most viral-coding sequences (those sequences encoding viral proteins), (2) the viral inverted terminal repeats (ITRs) which are sequences required for viral DNA replication, (3) up to 28-32 kb of "exogenous" or "heterologous" sequences (e.g., sequences encoding an ammonia producing enzyme), and (4) the viral DNA packaging sequence which is required for packaging of the viral genomes into infectious capsids. For specifically targeting liver, preferred variants of such recombinant adenoviral vectors contain tissue-specific enhancers and promoters operably linked to for example, SEQ ID NO: 1.

Other viral vectors that might be used in the invention are adeno-associated virus (AAV)-based vectors. AAV-based vectors are advantageous because they exhibit high transduction efficiency of target cells and can integrate into the host genome in a site-specific manner. Use of recombinant AAV vectors is discussed in detail in Tal, J., *J. Biomed. Sci.* 7:279-291, 2000 and Monahan and Samuski, *Gene Therapy* 7:24-30, 2000. A preferred AAV vector comprises a pair of AAV inverted terminal repeats which flank at least one cassette containing a tissue (e.g., gum)- or cell-specific promoter operably linked to a urease nucleic acid. The DNA sequence of the AAV vector, including the lilts, the promoter and, for example, urease gene may be integrated into the host genome.

The use of herpes simplex virus (HSV)-based vectors is discussed in detail in Cotter and Robertson, *Curr. Opin. Mol. Ther.* 1:633-644, 1999. HSV vectors deleted of one or more immediate early genes (IE) are advantageous because they are generally non-cytotoxic, persist in a state similar to latency in the host cell, and afford efficient host cell transduction. Recombinant HSV vectors can incorporate approximately 30 kb of heterologous nucleic acid. A preferred HSV vector is one that: (1) is engineered from HSV type I, (2) has its IE genes deleted, and (3) contains a tissue-specific promoter operably linked to a urease nucleic acid. HSV amplicon vectors may also be useful in various methods of the invention. Typically, HSV amplicon vectors are approximately 15 kb in length, and possess a viral origin of replication and packaging sequences.

Retroviruses such as C-type retroviruses and lentiviruses might also be used in the invention. For example, retroviral vectors may be based on murine leukemia virus (MLV). See, e.g., Hu and Pathak, *Pharmacol. Rev.* 52:493-511, 2000 and Fong et al., *Crit. Rev. Ther. Drug Carrier Syst.* 17:1-60, 2000. MLV-based vectors may contain up to 8 kb of heterologous (therapeutic) DNA in place of the viral genes.

Additional retroviral vectors that might be used are replication-defective lentivirus-based vectors, including human immunodeficiency (HIV)-based vectors. See, e.g., *Vigna* and Naldini, *J. Gene Med.* 5:308-316, 2000 and Miyoshi et al., *J. Virol.* 72:8150-8157, 1998. Lentiviral vectors are advantageous in that they are capable of infecting both actively dividing and non-dividing cells. They are also highly efficient at transducing human epithelial cells. Lentiviral vectors for use in the invention may be derived from human and non-human (including SIV) lentiviruses. Preferred lentiviral vectors include nucleic acid sequences required for vector propagation as well as a tissue-specific promoter operably linked to, for example, SEQ ID NO: 1, derivatives, variants and fragments thereof. These former may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), might also be used in the invention. Use of alphaviruses is described in Lundstrom, K., Intervirology 43:247-257, 2000 and Perri et al., Journal of Virology 74:9802-9807, 2000. Alphavirus vectors typically are constructed in a format known as a replicon. A replicon may contain (1) alphavirus genetic elements required for RNA replication, and (2) a heterologous nucleic acid such as one encoding SEQ ID NO: 1. Within an alphavirus replicon, the heterologous nucleic acid may be operably linked to a tissue-specific promoter or enhancer.

Recombinant, replication-defective alphavirus vectors are advantageous because they are capable of high-level heterologous (therapeutic) gene expression, and can infect a wide host cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a host cell. The replicons may also exhibit transient heterologous nucleic acid expression in the host cell. A preferred alphavirus vector or replicon is non-cytopathic.

In many of the viral vectors compatible with methods of the invention, more than one promoter can be included in the vector to allow more than one heterologous gene to be expressed by the vector. Further, the vector can comprise a sequence which encodes a signal peptide or other moiety which facilitates the secretion of a gene product from the host cell.

To combine advantageous properties of two viral vector systems, hybrid viral vectors may be used to deliver a nucleic acid to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral lilts may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the host cell genome and effect stable urease gene expression.

Other nucleotide sequence elements which facilitate expression of SEQ ID NO: 1, derivatives, variants and fragments thereof and cloning of the vector are further contemplated. For example, the presence of enhancers upstream of the promoter or terminators downstream of the coding region, for example, can facilitate expression.

Base Modifications

In another preferred embodiment, SEQ ID NO: 1 and/or poly (I:C) can be modified. Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to locked nucleic acids (LNA), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Primers composed, either in whole or in part, of nucleotides with universal bases are useful for reducing or eliminating amplification bias against repeated sequences in a target sample. This would be useful, for example, where a loss of sequence complexity in the amplified products is undesirable. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to $-O[(CH_2)_nO]_m CH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3]_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can comprise inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only comprise a single modification, but may also comprise multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science 254:1497-1500 (1991)).

In another preferred embodiment, the nucleobases of SEQ ID NO: 1, can be made up of different types of nucleotides or the same type of nucleotides. For example, one or more of the nucleotides can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can comprise bases (that is, the base portion of the nucleotide) and can (and normally will) comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. Cleavage, of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the T$_m$ of an oligonucleotide/target pair, which is the temperature at which the oligonucleotide and target dissociate; dissociation is detected spectrophotometrically. The higher the $T_m$, the greater the affinity of the oligonucleotide for the target. In a more preferred embodiment, SEQ ID NO: 1 comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher $T_m$ (i.e., higher target binding affinity) than; 2'-deoxyoligonucleotides against a given target. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. *Acc. Chem. Res.* 1995, 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$). The amide backbones disclosed by De Mesmaeker et al. *Acc. Chem. Res.* 1995, 28:366-374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). Oligonucleotides may also comprise one or more substituted sugar moieties. Preferred oligonucleotides comprise one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al., *Helv. Chim.*

*Acta,* 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2'deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Komberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-5-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethyleneglycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (ref: Recent advances in the medical chemistry of antisense oligonucleotide by Uhlman, Current Opinions in Drug Discovery & Development 2000 Vol 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 10 and 25 nucleotides, more preferably between about 12 and 20 nucleotides.

Non-Viral Delivery

In addition to viral vector-based methods, non-viral methods may also be used to introduce nucleic acid sequences into a host cell, such as described in the examples which follow. Alternate methods are described herein. A review of non-viral methods of gene delivery is provided in Nishikawa and Huang, *Human Gene Ther.* 12:861-870, 2001. For example, a non-viral gene delivery method according to the invention employs plasmid DNA to introduce a urease nucleic acid into a cell. Plasmid-based gene delivery methods are generally known in the art and are described in references such as Han, Y., *Curr. Opin. Mol. Ther.* 1:116-120, 1999, Wolff, J. A., *Neuromuscular Disord.* 7:314-318, 1997 and Arztl, Z., *Fortbild Qualitatssich* 92:681-683, 1998.

Methods involving physical techniques for introducing SEQ ID NO: 1, derivatives, fragments and variants thereof into a host cell can be adapted for use in the present invention. For example, the particle bombardment method of gene transfer utilizes an Accell device (gene gun) to accelerate DNA-coated microscopic gold particles into a target tissue. See, e.g., Yang et al., *Mol. Med. Today* 2:476-481 1996 and Davidson et al., *Rev. Wound Repair Regen.* 6:452-459, 2000. As another example, cell electropermeabilization (also termed cell electroporation) may be employed to deliver nucleic acids into cells. See, e.g., Preat, V., *Ann. Pharm. Fr.* 59:239-244 2001.

Synthetic gene transfer molecules can be designed to form multimolecular aggregates with plasmid DNA. These aggregates can be designed to bind to a target cell surface in a manner that triggers endocytosis and endosomal membrane disruption. For example, polymeric DNA-binding cations (including polylysine, protamine, and cationized albumin) are linked to cell-specific targeting ligands that trigger receptor-mediated endocytosis into the desired cell. See, e.g., Guy et al., *Mol. Biotechnol.* 3:237-248, 1995 and Garnett, M. C., *Crit. Rev. Ther. Drug Carrier Syst.* 16:147-207, 1999. Cationic amphiphiles, including lipopolyamines and cationic lipids, may be used to provide receptor-independent urease nucleic acid transfer into target cells. In addition, preformed cationic liposomes or cationic lipids may be mixed with plasmid DNA to generate cell-transfecting complexes. Methods involving cationic lipid formulations are reviewed in Feigner et al., *Ann. N.Y. Acad. Sci.* 772:126-139, 1995 and Lasic and Templeton, *Adv. Drug Delivery Rev.* 20:221-266, 1996. For gene delivery, DNA may also be coupled to an amphipathic cationic peptide (Fominaya et al., *J. Gene Med.* 2:455-464, 2000).

Methods that involve both viral and non-viral based components may be used according to the invention. For example, an Epstein Barr virus (EBV)-based plasmid for therapeutic gene delivery is described in Cui et al., *Gene Therapy* 8:1508-1513, 2001. Additionally, a method involving a DNA/ligand/polycationic adjunct coupled to an adenovirus is described in Curiel, D. T., *Nat. Immun.* 13:141-164, 1994.

Methods involving ultrasound contrast agent delivery vehicles may be used in the invention. See, e.g., Newman et al., *Echocardiography* 18:339-347, 2001 and Lewin et al. *Invest. Radiol.* 36:9-14, 2001. Gene-bearing microbubbles, which cavitate upon exposure to ultrasound, might be used to deliver the gene to a specific target tissue.

A natural or synthetic matrix that provides support for the delivered agent prior to delivery might be used in the invention. See, for example, the techniques described in Murphy and Mooney, *J. Period Res.*, 34:413-9, 1999 and Vercruysse and Prestwich, *Crit. Rev. Ther. Drug Carrier Syst.*, 15:513-55, 1998. Matrices suitable for use in the invention may be formed from both natural or synthetic materials and may be designed to allow for sustained release of the therapeutic agent and growth factors over prolonged periods of time. For implantation into an animal subject, a preferred matrix is resorbable and/or biocompatible (i.e., does not produce an adverse or allergic reaction when administered to the recipient host). In some embodiments of the invention, matrices are impregnated with growth factors capable of stimulating the chemotaxis and mobilization of stem cells.

DNA microencapsulation may be used to facilitate delivery of a SEQ ID NO: 1, derivatives variants and fragments thereof, for example. The nucleic acid can be delivered separately or in conjunction with the different components of the BiOmune composition. Microencapsulated gene delivery vehicles may be constructed from low viscosity polymer solutions that are forced to phase invert into fragmented spherical polymer particles when added to appropriate non-solvents. Methods involving microparticles are discussed in Hsu et al., *J. Drug Target* 7:313-323, 1999 and Capan et al., *Pharm. Res.* 16:509-513, 1999.

Methods involving microencapsulated recombinant cells may be used in the invention. Such an approach may be used in either in vivo or ex vivo techniques. Cells that contain an expression vector or that have been engineered to stably express SEQ ID NO: 1 gene products may be encapsulated in microcapsules that provide protection from immune mediators. Preferred microencapsulation particles, also referred to as encapsulation devices, consist of biocompatible and biodegradable components. Techniques involving microencapsulated cells are discussed in Ross et al. *Hum. Gen. Ther.* 11:2117-2127, 2000 and Fong et al., *Crit. Rev. Ther. Drug Carrier Syst.* 17:1-60, 2000.

Pharmaceutical Formulations and Modes of Administration

The composition of the invention can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, $18^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Some methods of delivery that may be used include: a. encapsulation in liposomes; b. transduction by retroviral vectors; c. localization to nuclear compartment utilizing nuclear targeting site found on most nuclear proteins; d. transfection of cells ex vivo with subsequent re-implantation or administration of the transfected cells, e. a DNA transporter system.

A nucleic acid sequence e.g., as that identified by SEQ ID NO: 1, may be administered utilizing an ex vivo approach whereby cells are removed from an animal, transduced with the peptide 35 nucleic acid sequence and reimplanted into the animal. The liver can be accessed by an ex vivo approach by removing hepatocytes from an animal, transducing the hepatocytes in vitro with the nucleic acid sequence and reimplanting them into the animal (e.g., as described for rabbits by Chowdhury et al, *Science* 254: 1802-1805, 1991, or in humans by Wilson, *Hum. Gene Ther.* 3: 179-222, 1992) incorporated herein by reference.

Many nonviral techniques for the delivery of a nucleic acid sequence into a cell can be used, including direct naked DNA uptake (e.g., Wolff et al., *Science* 247: 1465-1468, 1990), receptor-mediated DNA uptake, e.g., using DNA coupled to asialoorosomucoid which is taken up by the asialoglycoprotein receptor in the liver (Wu and Wu, *J. Biol. Chem.* 262: 4429-4432, 1987; Wu et al., *J. Biol. Chem.* 266: 14338-14342, 1991), and liposome-mediated delivery (e.g., Kaneda et al., *Expt. Cell Res.* 173: 56-69, 1987; Kaneda et al., *Science* 243: 375-378, 1989; Zhu et al., *Science* 261: 209-211, 1993). Many of these physical methods can be combined with one another and with viral techniques; enhancement of receptor-mediated DNA uptake can be effected, for example, by combining its use with adenovirus (Curiel et al., *Proc. Natl. Acad. Sci. USA* 88: 8850-8854, 1991; Cristiano et al., *Proc. Natl. Acad. Sci. USA* 90: 2122-2126, 1993).

BiOmune Compositions Comprising a Variety of Other Lectins

Lectins are carbohydrate-binding proteins of nonimmune origin that agglutinate cells or precipitate polysaccharides or glycoconjugates, i.e., proteins or lipids conjugated to oligo- or polysaccharides. They are widely distributed, and have been isolated from both plant and animal sources. Their reactions with living cells are based on their ability to bind with antibody-like specificity to particular arrangements of the sugar residues that make up oligo- or polysaccharides.

The surface of eukaryotic cells contain very numerous molecules of glycoproteins and glycolipids. Similarly, the cell walls of bacteria and the envelopes and capsids of viruses contain structural polysaccharides and/or glycoproteins. The carbohydrate moieties of these molecules which are displayed on the cell surfaces exhibit great variety in composition and structure that serves to distinguish the types of cells and to serve as a signal to other cells or materials which come into contact with the cell. For, example, variation in the carbohydrate moieties of glycoproteins in the membrane of red blood cells serves as the basis for the conventional blood typing classification. When lectins recognize and bind to certain carbohydrate moieties they may serve to cross-link and agglutinate the cells bearing the binding groups, a property that earns for them the alternate name of agglutinins.

In a preferred embodiment, the composition of the invention, e.g., BiOmune inhibits pathogens from attaching to a cell. Without wishing to be bound by theory, the same, sort of carbohydrate moieties often serve as attachment points for pathogens to bind to target cells and invade them, the compositions described herein may block infection of target cells by blocking the sites used by pathogens as recognition markers. The same type of specific binding occurs between sperm and egg in conception, and can be blocked by lectins. The binding ability of lectins may be very specific for certain mono- or oligosaccharides, allowing lectins to be used as a powerful tool for investigating the oligosaccharide epitopes on the surface of organisms or cells. Lectins can distinguish between blood cells of specific blood type, malignant from normal cells, and among species and genus of organisms. While glycoproteins, glycolipids, and bacterial cell walls are believed to be the main lectin-binding locations on the surface of cells, it is not excluded that carbohydrate moieties derived from other molecules or cellular structures may be displayed on the cell surface or that other lectin-binding structures may be present on cell surfaces. All such lectin-binding structures may be targets for the lectins used in the method of this invention.

In the context of this application the term microorganism includes any microscopic organism within the categories of algae, bacteria, fungi, protozoa, viruses, and subviral agents.

In another preferred embodiment, the BiOmune composition are used to identify infectious disease microorganisms in vitro and are also capable of binding to them in vivo, thereby preventing them from infecting living cells. Human disease-causing organisms (and the diseases caused by them) that can be bound by lectins include *Neisseria gonorrhoeae* (gonorrhoea); *Chlamydia trachomatis* (chlamydia, lymphogranuloma venereum); *Treponema pallidum* (syphilis); *Haemophilus ducrei* (chancroid); *Donovania granulomatis* (donovanosis); *Mycoplasma pneumoniae, M. hominis, M. genitalium, Ureaplasma urealyticum* (mycoplasmas); *Shigella flexneri* (shigella); *Salmonella typhi, S. choleraesuis, S. enteritidis* (salmonella); *Campylobacter fetus, C. jejuni* (campylobacter); human immunodeficiency virus HIV-1 and HIV-2 (HIV, AIDS); HTLV-1 (T-lymphotropic virus type 1); herpes simplex virus type 1 and type 2 (HSV-1 and HSV-2); Epstein-Barr virus; cytomegalovirus; human herpesvirus 6; varicella-zoster virus; human papillomaviruses (many types) (genital warts); *Molluscum contagiosum* (MSV); hepatitis A virus, hepatitis B virus (viral hepatitis); *Trichomoniasis vaginalis* (trichomoniasis); yeasts such as *Candida albicans* (vulvovaginal candidiasis). Other diseases that are transmitted by contact with bodily fluids may also be transmissible by sexual contact and are capable of being prevented by administration of BiOmune. Accordingly, the term sexually transmitted diseases (STD's) is to be interpreted in this application as including any disease that is capable of being transmitted in the course of sexual contact, whether or not the genital organs are the site of the resulting pathology.

Inasmuch as lectins are also capable of agglutinating human sperm and other components of the male ejaculate, and thereby rendering the sperm immobile, intravaginal administration of lectins can also serve as a method of contraception.

According to the invention a dose of BiOmune adapted to bind and agglutinate pathogenic microorganisms and/or block the recognition sites on target cells is administered to the vagina prior to sexual intercourse. The active ingredients may also include lectins capable of binding and/or inactivating sperm to serve as a contraceptive.

Because of the specificity of lectins for certain microorganisms, it is preferred to administer a mixture of lectins chosen for their properties of agglutinating specific pathogens. It is also according to the invention to administer a mixture of sperm-agglutinating lectins and lectins capable of binding to pathogenic organisms to provide simultaneous contraception and protection against infection.

A representative listing of lectins, the abbreviations by which they are referred to, and their sources is given in Table 6.

TABLE 6

Lectins and Abbreviations

| Lectin | Source |
|---|---|
| AAnA | *Anguilla anguilla* (Eel serum) |
| AAurA | *Aleuria aurantia* (Orange peel fungus) |
| ABA | *Agaricus bisporus* (Mushroom) |
| ABrA | *Amphicarpanea bracteata* (hog-peanut) |
| AL | *Hippaestrum hybrid* (Amaryllis bulbs) |
| APA | *Abrus precatorius* (Jequirity bean) |
| BPA | *Bauhinia purpurea alba* (camel's foot tree) |
| CAA | *Caragana arborescens* (Siberian pea tree) |
| ConA | *Concanavalia ensiformis* (Jack bean) |
| CPA | *Cicer arietinum* (chick pea) |
| CSA | *Cytisus scoparius* (Scotch broom) |
| DBA | *Colichos biflorus* (horse gram) |
| DSA | *Datura Stramonium* (Jimson weed, Thorn apple) |
| ECA | *Erythrina crystagalli* (Coral tree) |
| ECorA | *Erythrina coralldendron* (Coral tree) |
| EEA | *Euonymus europaeus* (spindle tree) |
| DBA | *Dolichos biflorus* (horse gram) |
| GNA | *Galanthus nivalis* (Snowdrop bulb) |
| GSA-1/GSA-II | *Griffonia simplicifolia* |
| HAA | *Helix aspersa* (Garden snail) |
| HPA | *Helix pomatia* (Roman or edible snail) |
| JAC (Jacalin) | *Artocarpus integrifolia* (jackfruit) |
| LAA | *Laburnum alpinum* |
| LBA | *Phaseolus lunatis* (also limensis) (Lima bean) |
| LCA (LcH) | *Lens culinaris* (lentil) |
| LEA | *Lycopersicon esculentum* (Tomato) |
| LOA | *Lathyrus oderatus* (Sweet pea) |
| LTA (LOTUS) | *Lotus tetragonolobus* (Asparagus pea) |
| MAA | *Maackla amurensis* (maackla) |
| MPA | *Maclura pomifera* (Osage orange) |
| NPL (NPA) | *Narcissus pseudonarcissus* (daffodil) |
| PAA | *Phytolacca americana* (Pokeweed) |
| PHA (PHA-L) | *Phaseolis vulgaris* (Red kidney bean) |
| PNA | *Arachis hypogaea* (Peanut) |
| PSA | *Pisum sativum* (Pea) |
| PWA | *Phytolacca americana* (pokeweed) |
| PTAgalactose | *Psophocarpus tetagonolobus* (Winged bean) |
| PTAgalNac | *Psophocarpus tetagonolobus* (winged bean) |
| RCA-I/RCA-II | *Ricinus communis* (Castor bean) |
| RPA | *Robinia pseudoaccacia* (black locust) |
| SBA | *Glycine max* (Soybean) |
| SJA | *Sophora japonica* (Japanese pagoda tree) |
| STA | *Solanum tuberosum* (Potato) |
| TKA | *Trichosanthes kinlowii* (China gourd) |
| UEA-I/UEA-II | *Ulex europaeus* (Gorse or Furz seeds) |
| VAA | *Viscum album* (European mistletoe) |
| VFA | *Vicia faba* (Fava bean) |
| VGA | *Vicia graminea* |
| VRA | *Vigna radiata* (mung bean) |
| VSA | *Vicia Sativa* |
| VVA | *Vicia villosa* (Hairy vetch) |
| WFA | *Wisteria floribunda* (Japanese wisteria) |
| WGA | *Triticum vulgaris* (Wheat germ) |
| suc-WGA | Succinyl WGA |

Thus, in accordance with the invention, the lectin *Helix pomatia* can be substituted with one or more lectins and/or used in addition with one or more lectins. Therefore, the BiOmune compositions can be tailored for preventative, therapy and treatment of a wide variety of disorders. For example, *N. gonorrheae* is agglutinated by lectins that bind to N-acetyl-D-glucosamine residues on their surfaces. Such lectins include WGA and STA, which are known to agglutinate all 193 clinical isolates of *N. gonorrheae*. WGA is effective for such agglutination at a concentration of 3.1 micrograms per milliliter. Other lectins showing some agglutination activity with respect to *N. gonorrheae* include RCA-I, RCA-II, GSA-I, and SBA.

Certain species of *Chlamydia* (*trachomatis, psittaci*, and *pneumoniae*) are known to be bound by the lectins ConA, DBA, UEA-1, SBA, and PNA. WGA also binds to the receptors on certain cells, thereby blocking infection by *C. trachomatis* and *C. psittaci*. PHA binds to several isolates of *H. ducrei*, suggesting that N-acetyl-D-glucosamine is present in the cell envelope polysaccharide. WGA has been found to agglutinate a variety of bacterial cells, including *Escherichia coli, Micrococcus luteus*, and some types of *Staphylococcus aureus*. WGA, specific for N-acetyl-D-glucosamine and SBA, specific for N-acetyl-D-galactosamine, are capable of agglutinating the many bacterial species which contain these sugar residues in their cell wall polysaccharides.

Various lectins are capable of binding to certain glycoproteins present in the envelope of HIV virus. For example, ConA has been found to block infection of certain cell lines against infection by HIV in vitro, and conglutinin, a lectin derived from bovine serum, has been found to bind to the HIV envelope precursor protein gp 160, thereby preventing attachment to CD-4 receptors of target cells in vitro. GNA has been found to prevent infection of T-cells by HIV in vitro. Consequently, ConA, GNA and WGA have been found to be effective at preventing infection of target cells by HIV-1 and HIV-2 in vitro. NPL and conglutinin have shown some activity as well.

HPA and ConA have demonstrated efficacy in the prevention of infection of target cells by HSV-1 and HSV-2.

Lectins are also useful in aggregation of sperm. PHA, WGA, STA, ConA, PSA, APA, ECA, ECorA have demonstrated varying degrees of efficacy in agglutination of sperm.

While the lectins discussed above and the organisms against which they are effective are representative of useful lectins according to the invention, it is to be understood that other lectins may be discovered which are active in the binding and agglutination of the pathogens infectious diseases, and that the use of such lectins is intended to be included within the scope of the invention.

The selection of particular lectins for use in the BiOmune compositions will depend on the diseases sought to be prevented. It is preferred to administer a mixture of lectins, each selected for best agglutinative efficacy against a particular pathogen. The lectins may be administered in any fluid or ointment vehicle suitable for topical administration of pharmaceutical compounds. Thus creams, ointments, foams, suppositories, ovules and the like may be formulated in which the selected lectins are dispersed in a non-toxic vehicle suitable for topical and in particular for vaginal administration. Such vehicles include white petrolatum, hydrophilic petrolatum, lanolin emulsions, polyethylene glycols, cocoa butter and the like. Useful vehicles include emollient oils such as water-soluble oils, e.g., liquid polyethylene glycols, which promote complete and uniform distribution of the medicament within the vagina. Representative suitable vehicles include a lubricating jelly comprised of water, propylene glycol, hydroxyethyl cellulose, benzoic acid and sodium hydroxide, a water-soluble oil comprised of water, glycerin, propylene glycol, polyquaternium #5, methyl paraben and propyl paraben; a cream comprised of benzyl alcohol, cetearyl alcohol, cetyl esters wax, octyldodecanol, polysorbate 60, purified water, and sorbitan monostearate; and a suppository comprised of polyethylene glycol (PEG) 18, PEG-32, PEG-20 stearate, benzethonium chloride, methyl paraben and lactic acid.

According to the invention, the dispersion, suspension, or solution of lectins in the vehicle may be applied to the site of a lesion, such as the lesions produced by tumors e.g., melanoma, infectious disease microorganisms such as herpes simplex virus type 1 or type 2, chancroid, genital warts, chancre of syphilis, and the like, to prevent the transfer of pathogens. The lectins may also be introduced into the vagina, in order to prevent conception or infection by pathogens introduced during sexual intercourse. The amount of lectins to be applied will be an amount that is effective to prevent conception or infection or substantially reduce the risk thereof. The amounts needed to achieve these goals will depend on the effectiveness of the individual lectins, their affinity for the target cell and the like. The effective amounts can be determined by the skilled practitioner by routine experimentation.

Also in accordance with the invention, the ability of different lectin to bind pathogenic micro-organisms, thereby interfering with their mobility, growth and reproduction, lectins are also useful in therapy of topical infections of the vagina. For those diseases wherein the pathogens grow and reproduce within the lumen of the vagina, administration of lectins, alone or in combination with other antimicrobial materials, can assist in the treatment and cure of the infection.

Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

EXAMPLES

The following examples serve to illustrate the invention without limiting it thereby. It will be understood that variations and modifications can be made without departing from the spirit and scope of the invention.

Example 1

Therapeutic Compositions

*Helix pomatia* lectin, is modified using 2,4-dinitrophenol (DNP). Modification is by coupling of DNP to the soluble protein. (Inman, J. K. et al., *Immunochemistry*, 10:165, 1973). A solution of 300 mg of *Helix pomatia* lectin in 4.0 ml of 0.25 M potassium borate was cooled to 0° C. Fifty seven micromoles (28.6 mg of N-(2,4-dinitrophenyl-β-alanylglycylglycine Boc hydrazide (compound "J") were converted to the corresponding acyl azide by reaction with nitrous acid in cold dimethylformamide after removal of the Boc group.

After addition of sulfamic acid to destroy nitrous acid, the azide solution was added to the cold buffered *Helix pomatia*. The mixture was stirred at 0° C. for 2 days and dialyzed in the cold for 2 days against 0.1 M NaCl and 2 days against water. Outside solutions were saturated with toluene. The dialysate was lyophilized.

The resulting *Helix pomatia* lectin has about 10 DNP molecules attached to primarily lysine residues in the lectin molecule. This hapten conjugate is added to compound A. Compound A comprises isolated pokeweed mitogen which is coated with polyethylene glycol as described in U.S. patent application Ser. No. 09/983,129 which is incorporated herein by reference in its entirety. Compound A optionally comprises recombinant Interleukin 2 (rIL-2) of about 100,000 U/kg.

The resultant composition comprises polyethylene glycol coated pokeweed mitogen (PWM-PEG) of 10 µg PWM protein/kg; *Helix pomatia* lectin coupled to hapten DNP(HPL-DNP) of 30 µg/HPL protein/kg and recombinant Interleukin 2 (rIL-2) of 100,000 U/kg.

Compound B comprises a DNA nucleotide: GACGTC-GACGTTAACGTCAACGTT (SEQ ID NO: 1); DOTAP (1,2 dioleoyl-3-trimethylammonium-propane) and cholesterol.

Compound B is prepared as follows. DNA (SEQ ID NO: 1) is added to cationic lipids DOTAP and cholesterol in a 1:1 molar ratio. The DNA is added at a ratio of 30 nmol lipid to 1 µg DNA to a final concentration of 100 µg DNA per 0.1 ml dextrose. The dose of DNA used for immunostimulation is about 50-100 µg/kg.

The resulting composition is herein termed BiOmune.

Example 2

Treatment of Cancer

Protocol for treatment of breast cancer: Patient groups include women with breast cancer who have recurrent local disease or primary local disease. These women must have either not undergone chemotherapy, or are at least six weeks post chemotherapy. These women will be given systemic immune stimulation, and a breast poultice in the form of a cream. The cream will contain the Helix Lectin or a placebo. The study will be double blinded, with the stipulation that the study will be unblinded if one group shows an early advantage over the other.

Workup of the patients will consist of History and Physical exams, routine labs, color photographs of the affected breast (s). Initial NMR, PET scans and thermography will be employed to evaluate the primary and the distant lesions. The patients will be given a six-week course of therapy. On the completion of therapy, the initial scans will be repeated. The patients will then be graded as to response.

Cost: A six-week course of therapy will cost about one thousand dollars per patient for material to make the BiOmune cream. The cost of material for the injectable or the oral version of BiOmune would be about $2000/patient. The cost for medical tests and supervision is estimated at $ 6,000 per patient. If we ran 100 patients through this protocol, we would need close to one million dollars. This is a very small amount for a treatment, which we believe, will revolutionize the treatment of breast cancer.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All references mentioned herein, are incorporated by reference in pertinent part.

What is claimed is:

1. A method of treating a cancer patient, comprising:
   administering to a patient in need thereof, a composition comprising an isolated nucleic acid molecule and a mitogen coated with polyethylene glycol, wherein the isolated nucleic acid molecule comprises SEQ ID NO:1;
   contacting a tumor cell with the composition resulting in the lysis of the tumor cell;
   thereby treating the patient.

2. A method of inhibiting immunoglobulin isoclass switching in at least one of a cancer patient and a patient suffering from an infectious disease organism, comprising:
   administering to a patient in need thereof, a composition comprising an isolated nucleic acid molecule and a mitogen coated with polyethylene glycol, wherein the isolated nucleic acid molecule comprises SEQ ID NO:1;
   contacting at least one of a tumor cell and an infected cell with the composition resulting in the lysis of the cells;
   thereby treating the patient.

3. The method of claim 2, wherein immunoglobulin M (IgM) is inhibited from switching to immunoglobulin G (IgG).

4. The method of claim 3, wherein the IgM fixes complement on at least one of a tumor and an infected cell.

5. The method of claim 1, wherein the composition is administered orally.

6. The method of claim 2, wherein the composition is administered orally.

7. The method of claim 1, wherein the tumor cell is a lymphoma cell.

8. The method of claim 2, wherein the patient is a cancer patient and the tumor cell is a lymphoma cell.

9. The method of claim 1, wherein the mitogen is pokeweed mitogen or Jewelweed mitogen.

10. The method of claim 2, wherein the mitogen is pokeweed mitogen or Jewelweed mitogen.

* * * * *

```
                               SEQUENCE LISTING

<160> NUMBER OF SEQ ID NOS: 1

<210> SEQ ID NO 1
<211> LENGTH: 24
<212> TYPE: DNA
<213> ORGANISM: Artificial sequence
<220> FEATURE:
<223> OTHER INFORMATION: synthetic construct

<400> SEQUENCE: 1
gacgtcgacg ttaacgtcaa cgtt                                                24
```